United States Patent
Kobayashi et al.

(10) Patent No.: US 10,130,610 B2
(45) Date of Patent: *Nov. 20, 2018

(54) ANTIMYCOTIC PHARMACEUTICAL COMPOSITION

(75) Inventors: Hirokazu Kobayashi, Yokohama (JP); Eiko Kosugi, Yokohama (JP); Nobuo Kubota, Yokohama (JP)

(73) Assignees: Pola Pharma Inc., Tokyo (JP); Nihon Nohyaku Co., Ltd., Tokyo (JP)

( * ) Notice: Subject to any disclaimer, the term of this patent is extended or adjusted under 35 U.S.C. 154(b) by 54 days.

This patent is subject to a terminal disclaimer.

(21) Appl. No.: 13/258,114

(22) PCT Filed: Apr. 9, 2010

(86) PCT No.: PCT/JP2010/056881
§ 371 (c)(1),
(2), (4) Date: Sep. 21, 2011

(87) PCT Pub. No.: WO2010/117089
PCT Pub. Date: Oct. 14, 2010

(65) Prior Publication Data
US 2012/0014893 A1  Jan. 19, 2012
US 2013/0011351 A2  Jan. 10, 2013

(30) Foreign Application Priority Data

Apr. 9, 2009 (JP) ................................. 2009-111551
Apr. 9, 2009 (JP) ................................. 2009-111552

(51) Int. Cl.
| | | |
|---|---|---|
| A61K 31/4178 | (2006.01) | |
| A61K 9/00 | (2006.01) | |
| A61K 9/08 | (2006.01) | |
| A61K 9/70 | (2006.01) | |
| A61K 47/08 | (2006.01) | |
| A61K 47/10 | (2017.01) | |
| A61K 47/14 | (2017.01) | |

(52) U.S. Cl.
CPC ........ *A61K 31/4178* (2013.01); *A61K 9/0014* (2013.01); *A61K 9/08* (2013.01); *A61K 9/7015* (2013.01); *A61K 47/08* (2013.01); *A61K 47/10* (2013.01); *A61K 47/14* (2013.01)

(58) Field of Classification Search
None
See application file for complete search history.

(56) References Cited

U.S. PATENT DOCUMENTS

| | | |
|---|---|---|
| 4,267,169 A | 5/1981 | Kamishita et al. |
| 4,636,520 A | 1/1987 | Umio et al. |
| 4,764,381 A | 8/1988 | Bodor et al. |
| 5,340,836 A | 8/1994 | Reinhard et al. |
| 5,461,068 A | 10/1995 | Thaler et al. |
| 5,690,923 A | 11/1997 | De Vringer et al. |
| 5,753,256 A | 5/1998 | Cordes et al. |
| 5,814,305 A | 9/1998 | Laugier et al. |
| 5,962,536 A | 10/1999 | Komer |
| 5,993,787 A | 11/1999 | Sun et al. |
| 6,007,791 A | 12/1999 | Coombes et al. |
| 6,008,256 A | 12/1999 | Haraguchi et al. |
| 6,017,920 A | 1/2000 | Kamishita et al. |
| 6,083,518 A | 7/2000 | Lindahl |
| 6,428,654 B1 | 8/2002 | Cronan, Jr. et al. |
| 6,585,963 B1 | 7/2003 | Quan et al. |
| 6,740,326 B1 | 5/2004 | Meyer et al. |
| 8,039,452 B2 * | 10/2011 | Sasagawa et al. ............ 514/183 |
| 8,980,931 B1 | 3/2015 | Masuda et al. |
| 2003/0017207 A1 | 1/2003 | Lin et al. |
| 2003/0235541 A1 | 12/2003 | Maibach et al. |
| 2004/0208906 A1 | 10/2004 | Tatara et al. |
| 2005/0232879 A1 | 10/2005 | Sasagawa et al. |
| 2006/0140984 A1 | 6/2006 | Tamarkin et al. |
| 2007/0099932 A1 | 5/2007 | Shirouzu et al. |
| 2008/0031835 A1 | 2/2008 | Kawamura et al. |
| 2008/0260656 A1 | 10/2008 | Mallard |
| 2009/0030059 A1 | 1/2009 | Miki et al. |
| 2009/0076109 A1 | 3/2009 | Miki et al. |
| 2009/0099202 A1 | 4/2009 | Shirouzu et al. |
| 2009/0137651 A1 | 5/2009 | Kobayashi et al. |
| 2009/0202602 A1 | 8/2009 | Ishima et al. |

(Continued)

FOREIGN PATENT DOCUMENTS

| | | |
|---|---|---|
| EP | 0 070 525 | 1/1983 |
| EP | 0 440 298 | 8/1991 |

(Continued)

OTHER PUBLICATIONS

Koga et al. ("In vitro antifungal activities of luliconazole, a new topical imidazole." Med. Mycol. 2009, 47(6), 640-647).*

(Continued)

*Primary Examiner* — Bethany P Barham
*Assistant Examiner* — Barbara S Frazier
(74) *Attorney, Agent, or Firm* — Knobbe, Martens, Olson & Bear, LLP

(57) ABSTRACT

In a pharmaceutical composition for external use containing a compound such as luliconazole and/or a salt thereof in an amount of 5% by mass or more, comprised is/are acetone, a polyoxyethylene alkyl (having 8 to 30 carbon atoms) ether, and/or a polyoxyethylene alkenyl (having 8 to 30 carbon atoms) ether. Provided is a preparation using a solvent other than crotamiton, propylene carbonate, and N-methyl-2-pyrrolidone as a solvent for solubilization and steric stabilization and having the following properties: 1) when a compound represented by the general formula (1) and/or a salt thereof has a stereoisomer, the amount of the stereoisomer of the compound and/or a salt thereof produced under a preservation condition of 60° C. for 3 weeks is 1% by mass or less with respect to the total mass of the compound and/or a salt thereof at the beginning of preservation; 2) the preparation is in a clear liquid state when preserved at a constant temperature of 20° C. immediately after manufacture; and 3) no crystal is deposited when the preparation is preserved at 5° C. for 2 weeks after manufacture.

5 Claims, No Drawings

(56) References Cited

U.S. PATENT DOCUMENTS

| | | |
|---|---|---|
| 2010/0168200 A1 | 7/2010 | Masuda et al. |
| 2010/0173965 A1 | 7/2010 | Masuda et al. |
| 2010/0204293 A1 | 8/2010 | Masuda et al. |
| 2010/0210702 A1 | 8/2010 | Vontz et al. |
| 2010/0210703 A1 | 8/2010 | Vontz et al. |
| 2010/0249202 A1 | 9/2010 | Koga et al. |
| 2012/0022120 A1 | 1/2012 | Kobayashi et al. |
| 2012/0149745 A1 | 6/2012 | Kobayashi et al. |
| 2013/0090365 A1 | 4/2013 | Kubota et al. |
| 2014/0080882 A1 | 3/2014 | Masuda et al. |

FOREIGN PATENT DOCUMENTS

| | | |
|---|---|---|
| EP | 0 715 856 | 6/1996 |
| EP | 1 138 314 | 10/2001 |
| EP | 1 522 316 | 4/2005 |
| EP | 1 537 868 | 6/2005 |
| EP | 1 637 132 | 3/2006 |
| EP | 2 005 958 | 12/2008 |
| EP | 2 005 959 | 12/2008 |
| EP | 2 025 337 | 2/2009 |
| EP | 2 191 827 | 6/2010 |
| JP | 61-118315 | 6/1986 |
| JP | 62-093227 | 4/1987 |
| JP | 62-223163 | 10/1987 |
| JP | 01-242525 | 9/1989 |
| JP | 01-246219 | 10/1989 |
| JP | 02-264723 | 10/1990 |
| JP | 02-275877 | 11/1990 |
| JP | 05-306223 | 11/1993 |
| JP | 06-199701 | 7/1994 |
| JP | 06-211651 | 8/1994 |
| JP | 07-188027 | 7/1995 |
| JP | 7-74144 | 8/1995 |
| JP | 07-206711 | 8/1995 |
| JP | 07-223971 | 8/1995 |
| JP | 08-020527 | 1/1996 |
| JP | 08-291049 | 11/1996 |
| JP | 10-152433 | 6/1998 |
| JP | 10-226639 | 8/1998 |
| JP | 10-226686 | 8/1998 |
| JP | 2001-064206 | 3/2001 |
| JP | 2001-316247 | 11/2001 |
| JP | 2002-114680 | 4/2002 |
| JP | 2002-193755 | 7/2002 |
| JP | 2002-284702 | 10/2002 |
| JP | 2002-363070 | 12/2002 |
| JP | 2003-252798 | 9/2003 |
| JP | 2004-529923 | 9/2004 |
| JP | 2005-154306 | 6/2005 |
| JP | 2005-239678 | 9/2005 |
| JP | 2005-289879 | 10/2005 |
| JP | 2005-298388 | 10/2005 |
| JP | 2005-298635 | 10/2005 |
| JP | 2006-028123 | 2/2006 |
| JP | 2006-232856 | 9/2006 |
| JP | 2006-306734 | 11/2006 |
| JP | 2007-091661 A | 4/2007 |
| WO | WO 90/14094 | 11/1990 |
| WO | WO 95/30440 | 11/1995 |
| WO | WO 96/11710 | 4/1996 |
| WO | WO 96/40047 | 12/1996 |
| WO | WO 97/02821 | 1/1997 |
| WO | WO 97/07794 | 3/1997 |
| WO | WO 00/01384 | 1/2000 |
| WO | WO 02/062336 | 8/2002 |
| WO | WO 02/083084 | 10/2002 |
| WO | WO 02/087570 | 11/2002 |
| WO | WO 03/020248 | 3/2003 |
| WO | WO 03/105841 | 12/2003 |
| WO | WO 2004/021968 | 3/2004 |
| WO | WO 2004/084826 | 10/2004 |
| WO | WO 2004/091521 | 10/2004 |
| WO | WO 2006/038317 | 4/2005 |
| WO | WO 2005/099764 | 10/2005 |
| WO | WO 2005/123136 | 12/2005 |
| WO | WO 2007/042682 | 4/2007 |
| WO | WO 2007/102241 | 9/2007 |
| WO | WO 2007/102242 | 9/2007 |
| WO | WO 2007/077806 | 12/2007 |
| WO | WO 2008/075207 | 6/2008 |
| WO | WO 2009/031642 A1 | 3/2009 |
| WO | WO 2010/093992 | 8/2010 |
| WO | WO 2014/041708 A1 | 3/2014 |
| WO | WO 2014/041825 A1 | 3/2014 |
| WO | WO 2014/041846 A | 3/2014 |
| WO | WO 2014/042043 A1 | 3/2014 |
| WO | WO 2014/136282 | 9/2014 |

OTHER PUBLICATIONS

GHS Classification Guidance for Enterprises (2$^{nd}$ Edition, Ministry of Economy, Trade and Industry, Japan, Mar. 2010.

Crotamiton Properties (http://www.chemspider.com/Chemical-Structure.2780.html) 2 pages, accessed Dec. 6, 2011.

Absolute ethanol MSDS (www.sciencelab.com/msds.php?msdsId=9923955) 7 pages, last updated Oct. 9, 2005.

Methyl Ethyl Ketone MSDS (www.sciencelab.com/msds.php?msdsId=9927358) 6 pages, last updated Nov. 1, 2010.

Niwano, et al. "Lanoconazole and Its Related Optically Active Compound NND-502: Novel Antifungal Imidazoles with a Ketene Dithioacetal Structure," *Current Medicinal Chemistry*, vol. 2, pp. 147-160, 2003.

Borrás-Blasco, et al. "A Mathematical Approach to Predicting the Percutaneous Absorption Enhancing Effect of Sodium Lauryl Sulphate," *International Journal of Pharmaceutics*, vol. 269, pp. 121-129, 2004.

Uchida, et al. "In vitro Activity of Novel Imidazole Antifungal Agent NND-502 Against *Malassezia* Species," *International Journal of Antimicrobial Agents*, vol. 21, pp. 234-238, 2003.

Uchida, et al. "In vitro Antifungal Activity of Luliconazole (NND-502), a Novel Imidazole Antifungal Agent," *Journal of Infectious Chemothererapy*, vol. 10, pp. 216-219, 2004.

Costa Martins, et al "In vitro Sensitivity of Dermatophytes to Urea," *Clinics*, vol. 61, No. 1, pp. 9-14, 2006.

www.babymd.com (available online as of Feb. 16, 2001 as evidenced by the attached Internet Archive report) accessed online Dec. 18, 2010.

Niwano, et al. "Efficacy of NND-502, a Novel Imidazole Antimycotic Agent, in Experimental Models of *Candida albicans* and *Aspergillus fumigatus* Infections," *International journal of Antimicrobial Agents*, vol. 12, pp. 221-228, 1999.

Niwano, et al. "In vitro and in vivo Antidermatophyte Activities of NND-4502, a Novel Optically Active Imidazole Antimycotic Agent," *Antimicrobial Agents and Chemotherapy*, vol. 42, No. 4, pp. 967-970, Apr. 1998.

Vieira, et al. "Cationic Lipids and Surfactants as Antifungal Agents: Mode of Action," *Journal of Antimicrobial Chemotherapy*, Vo. 58, pp. 760-767, 2006.

SDS Density downloaded from www.chemicalbook.com/ChemicalProductProperty_EN_CB2147453.htm, 2 pages, copyright 2010.

Pluronics Density downloaded from www.chemicalbook.com/ChemicalProductPropertyEN_Cb2709101.htm, 2 pages, copyright 2010.

Ethyl Cellulose Density downloaded from www.chemicalbook.com/ProductMSDSDetailCB6165620_EN.htm, 3 pages, copyright 2008.

International Search Report dated Oct. 18, 2010 issued to international application No. PCT/JP2010/056881.

Database WPI Week 200732, AN 2007-337919 and JP 2007-091661.

International Search Report dated Oct. 15, 2010 issued to international application No. PCT/JP2010/056884.

International Search Report dated Oct. 18, 2010 issued to international application No. PCT/JP2010/063230.

\* cited by examiner

ANTIMYCOTIC PHARMACEUTICAL COMPOSITION

CROSS-REFERENCE TO RELATED APPLICATIONS

This application is the U.S. National Phase under 35 U.S.C. § 371 of International Application PCT/JP2010/056881, filed Apr. 9, 2010, which claims priority to JP Application No. 2009-111551, filed Apr. 9, 2009 and JP 2009-111552, filed Apr. 9, 2009.

TECHNICAL FIELD

The present invention relates to a pharmaceutical composition, and more specifically, to an antimycotic pharmaceutical composition for external use useful for treatment of mycoses.

BACKGROUND ART

A compound represented by the general formula (1) as typified by, for example, luliconazole has an excellent antimycotic activity, and it has been pointed out that the compound may be applied to treatment of onychomycosis, which could not be treated by external administration hitherto (for example, see Patent document 1). However, in the case of producing such formulation for treatment of onychomycosis, there is a demand to further increase the content of the compound represented by the general formula (1) solubilized in the formulation. In particular, in a formulation for treatment of tinea unguium, it has been desired to solubilize the compound represented by the general formula (1) as typified by luliconazole in an amount twice or more that of a general formulation used for treatment of dermatomycosis, specifically, in an amount of 5% by mass or more, and it has been desired to develop a solvent for solubilizing and formulating the compound represented by the general formula (1) in a high concentration. However, there was a situation in which only a few solvents could be used for producing a formulation containing such compound in a high concentration because of its high crystallinity. That is, some kinds of solvents caused deficiency including crystal deposition when a low temperature condition such as 5° C. and crystal deposition during application.

In addition, in a solution of luliconazole or the like, there exists a situation in which stereoisomers are easily produced. Only crotamiton, propylene carbonate, and N-methyl-2-pyrroridone have been known as a solvent for preventing production of such stereoisomers (for example, see Patent document 2). However, such solvents may also be blended in a limited amount because of medicinal effects such as anti-inflammatory effects inherently possessed by the solvents, and it has been desired to develop a novel solvent for a formulation of luliconazole or the like as an alternative of the solvents.

General formula (1)

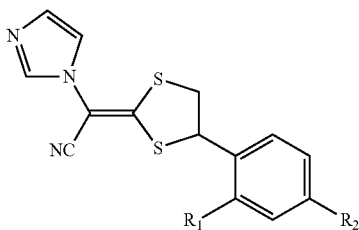

where $R_1$ and $R_2$ each independently represent a hydrogen atom or a halogen atom, and at least one of $R_1$ and $R_2$ represent a halogen atom.

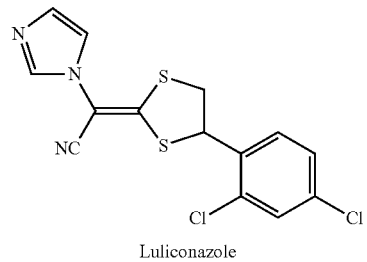 [SMILES: N#C/C(=C1/SCC(c2ccc(Cl)cc2Cl)S1)n1ccnc1]

Luliconazole

That is, there has been a demand to develop a solvent that enables a preparation having the following properties by means independent of solvent properties of crotamiton, propylene carbonate, and N-methyl-2-pyrrolidone (solubilization and steric stabilization properties of luliconazole or the like), in a pharmaceutical composition for external use containing luliconazole or the like in an amount of 5% by mass or more:

1) the amount of a stereoisomer of luliconazole or the like produced under a preservation condition of 60° C. for 3 weeks is 1% by mass or less with respect to the total mass of luliconazole or the like at the beginning of preservation;
2) the preparation is in a clear liquid state when preserved at a constant temperature of 20° C. immediately after manufacture.
3) no crystal is deposited when the preparation is preserved at 5° C. for 2 weeks after manufacture.

Meanwhile, acetone has been already used in an antimycotic pharmaceutical for external use, especially a pharmaceutical for external use for tinea unguium (for example, see Patent documents 3, 4 and 5). However, there has been no finding that acetone serves as a solvent for stably solubilizing luliconazole or the like while maintaining a steric structure of luliconazole or the like, in the pharmaceutical composition for external use containing luliconazole or the like.

[Patent document 1] WO/2007/102241
[Patent document 2] WO/2007/102242
[Patent document 3] JP 08-291049 A
[Patent document 4] JP 2009-511553 A
[Patent document 5] JP 2001-316247 A

SUMMARY OF INVENTION

Technical Problem

The present invention has been made under such circumstances, and an object of the present invention is to provide a preparation having the following properties 2) and 3) by means independent of solvent properties of crotamiton, propylene carbonate, and N-methyl-2-pyrrolidone (solubilization and steric stabilization properties of a compound represented by the general formula (1) and/or a salt thereof) in a pharmaceutical composition for external use containing the compound represented by the general formula (1) and/or a salt thereof such as luliconazole in an amount of 5% by mass or more. Further, when the compound represented by the general formula (1) and/or a salt thereof has a stereoisomer, an object of the present invention is to provide a preparation having the following properties 1) to 3):
1) the amount of a stereoisomer of the compound represented by the general formula (1) and a salt thereof produced under a preservation condition of 60° C. for 3 weeks is 1% by mass or less with respect to the total mass of the compound represented by the general formula (1) and/or a salt thereof at the beginning of preservation;
2) the preparation is in a clear liquid state when preserved at a constant temperature of 20° C. immediately after manufacture; and
3) no crystal is deposited when the preparation is preserved at 5° C. for 2 weeks after manufacture.

Solution to Problems

In view of such circumstances, the inventors of the present invention have intensively studied to seek a preparation having stable solubilizing properties by means independent of solvent properties of crotamiton, propylene carbonate, and N-methyl-2-pyrrolidone (solubilization and steric stabilization properties of a compound represented by the general formula (1) and/or a salt thereof) in a pharmaceutical composition for external use containing a compound represented by the general formula (1) and/or a salt thereof in an amount of 5% by mass or more. As a result, the inventors have found that such preparation is obtained by using acetone and/or a polyoxyethylene alkyl (or alkenyl) ether (note that the alkyl group and the alkenyl group have 8 to 30 carbon atoms) in place of crotamiton, propylene carbonate, and N-methyl-2-pyrrolidone. Thus, the present invention has been completed. That is, the present invention is as described below.
[1] A pharmaceutical composition for external use, comprising: 1) a compound represented by the following general formula (1) and/or a salt thereof in an amount of 5 to 15% by mass with respect to a total amount of the pharmaceutical composition; and 2) one kind or two or more kinds selected from the following group: acetone in an amount of 1 to 30% by mass with respect to a total amount of the pharmaceutical composition; a polyoxyethylene alkyl (having 8 to 30 carbon atoms) ether in an amount of 1 to 10% by mass with respect to a total amount of the pharmaceutical composition; and a polyoxyethylene alkenyl (having 8 to 30 carbon atoms) ether in an amount of 1 to 10% by mass with respect to a total amount of the pharmaceutical composition;

General formula (1)

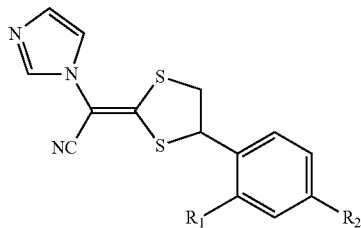

where $R_1$ and $R_2$ each independently represent a hydrogen atom or a halogen atom, and at least one of $R_1$ and $R_2$ represent a halogen atom.
[2] The pharmaceutical composition for external use according to the item [1], wherein the compound represented by the general formula (1) is luliconazole.

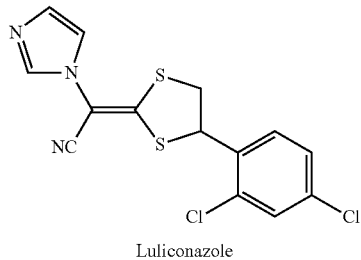

Luliconazole

[3] The pharmaceutical composition for external use according to the item [1] or [2], which has the following properties:
1) when the compound represented by the general formula (1) and/or a salt thereof has a stereoisomer, the amount of the stereoisomer of the compound and/or a salt thereof produced under a preservation condition of 60° C. for 3 weeks is 1% by mass or less with respect to the total mass of the compound and/or a salt thereof at the beginning of preservation;
2) the composition is in a clear liquid state when preserved at a constant temperature of 20° C. immediately after manufacture; and
3) no crystal is deposited when the composition is preserved at 5° C. for 2 weeks after manufacture.
[4] The pharmaceutical composition for external use according to any one of the items [1] to [3], further comprising one kind or two or more kinds selected from a diester carbonate, an aromatic alcohol, and a diester of a dibasic acid, provided that a carbonic acid is excluded, in an amount of 1 to 30% by mass with respect to a total amount of the pharmaceutical composition.
[5] The pharmaceutical composition for external use according to any one of the items [1] to [4], in which the pharmaceutical composition is a medicament for treatment of tinea unguium.
[6] A method of manufacturing the pharmaceutical composition for external use according to any one of the items [1] to [5], comprising the steps of: mixing a compound represented by the general formula (1) and/or a salt thereof with a part of a solvent; after the previous process, adding components except acetone, a polyoxyethylene alkyl (having 8 to 30 carbon atoms) ether, and a polyoxyethylene alkenyl (having 8 to 30 carbon atoms) ether; and after the previous process, adding one kind or two or more kinds selected from acetone, a polyoxyethylene alkyl (having 8 to 30 carbon atoms) ether, and a polyoxyethylene alkenyl (having 8 to 30 carbon atoms) ether under a heating condition.

Advantageous Effects of Invention

According to the present invention, in the pharmaceutical composition for external use containing a compound represented by the general formula (1) and/or a salt thereof such as luliconazole in an amount of 5% by mass or more, there can be provided a preparation having the following properties 2) and 3) by means independent of solvent properties of crotamiton, propylene carbonate, and N-methyl-2-pyrrolidone (solubilization and steric stabilization properties of the compound represented by the general formula (1) and/or a salt thereof). Further, when the compound represented by the general formula (1) has a stereoisomer, an object of the present invention is to provide a preparation having the following properties 1) to 3):
1) the amount of a stereoisomer of the compound and/or a salt thereof represented by the general formula (1) and/or a salt thereof produced under a preservation condition of 60° C. for 3 weeks is 1% by mass or less with respect to the total mass of the compound and/or a salt thereof at the beginning of preservation;
2) the preparation is in a clear liquid state when preserved at a constant temperature of 20° C. immediately after manufacture; and
3) no crystal is deposited when the preparation is preserved at 5° C. for 2 weeks after manufacture.

DESCRIPTION OF EMBODIMENTS

<1> Compound Represented by the General Formula (1) and/or Salt Thereof as Essential Component of Pharmaceutical Composition for External Use of the Present Invention The pharmaceutical composition for external use of the present invention is characterized by including a compound represented by the general formula (1) and/or a salt thereof such as luliconazole and lanoconazole. Luliconazole is a compound represented by the chemical name (R)-(−)-(E)-[4-(2,4-dichlorophenyl)-1,3-dithiolan-2-ylidene]-1-imidazolylacetonitrile, and lanoconazole is a compound represented by the chemical name (±)-(E)-[4-(2-chlorophenyl)-1,3-dithiolan-2-ylidene]-1-imidazolylacetonitrile. Methods of manufacturing such compounds have already been known (see, for example, Japanese Patent Application Laid-open No. 09-100279).

The pharmaceutical composition for external use of the present invention is characterized by containing a compound represented by the general formula (1) and/or a salt thereof in an amount of generally 5 to 15% by mass, or preferably 8 to 13% by mass with respect to the total amount of the pharmaceutical composition. Luliconazole has excellent crystallinity, and thus, may cause crystal deposition in a content of 1% by mass or more when preserved using some kinds of solvents at a low temperature such as 5° C., even in a state where crystallization is suppressed by adding a hydroxycarboxylic acid such as lactic acid. In the present invention, such deposition is suppressed by using a combination of solvents of acetone and/or a polyoxyethylene alkyl (or alkenyl)ether as described below, thereby the bioavailability, in particular, transfer into the nail is enhanced and as a result a therapeutic effect for tinea unguium is enhanced. The nail is an organ where the transfer into the tissue is difficult, and in order to transfer an effective amount of a compound, the content is preferably 5% by mass or more, or more preferably 8% by mass or more with respect to the total amount of the pharmaceutical composition. Further, in view of the upper limit for suppressing crystal deposition at a low temperature, the content is preferably 15% by mass or less, or more preferably 13% by mass or less with respect to the total amount of the pharmaceutical composition. From the foregoing, the content is more preferably about 8 to 13% by mass.

The above-mentioned "salt thereof" is not particularly limited as long as it is physiologically acceptable. For example, there may be suitably given: mineral acid salts such as a hydrochloride, a nitrate, a sulfate, and a phosphate; organic acid salts such as a citrate, an oxalate, a lactate, and an acetate; and sulfate-containing salts such as a mesilate and a tosilate. In terms of safety and solubility, a hydrochloride is more preferred.

<2> Acetone and Polyoxyethylene Alkyl (or Alkenyl) Ether as Essential Components in Pharmaceutical Composition for External Use of the Present Invention The pharmaceutical composition for external use of the present invention is characterized by including acetone and/or a polyoxyethylene alkyl (or alkenyl)ether as essential components. The pharmaceutical composition is characterized by containing acetone in an amount of generally 1 to 30% by mass, or preferably 3 to 20% by mass with respect to the total amount of the pharmaceutical composition, a polyoxyethylene alkyl (or alkenyl)ether having an alkyl group or an alkenyl group with 8 to 30 carbon atoms, or preferably an alkyl group or an alkenyl group with 10 to 18 carbon atoms, or one kind or two or more kinds selected from respectively from a polyoxyethylene alkyl ether or a polyoxyethylene alkenyl ether in an amount of generally 1 to 10% by mass, or preferably 2 to 5% by mass with respect to the total amount of the pharmaceutical composition. That is, for such components, any one kind of the acetone and/or polyoxyethylene alkyl (or alkenyl)ether may be contained, or two kinds thereof (acetone and polyoxyethylene alkyl ether, or acetone and polyoxyethylene alkenyl ether) may be contained. The preferred content in the case where two kinds are contained may be understood as the sum of preferred contents of the respective components. This is because the effects thereof are independent of each other.

For an alkyl group or an alkenyl group of which the polyoxyethylene alkyl (or alkenyl)ether is formed, the group has 8 to 30 carbon atoms, or preferably 10 to 18 carbon atoms. To be specific, there may be particularly suitably exemplified a lauryl group, a cetyl group, an isostearyl group, and an oleyl group. In addition, the polymerization degree of oxyethylene in a polyoxyethylene group is preferably 1 to 30, or more preferably 2 to 25. For the properties, it is preferred that the polyoxyethylene alkyl (alkenyl)ether be in a liquid state under a condition of 1 atm and 25° C. For specific examples of the polyoxyethylene alkyl (or alkenyl) ether, there may be suitably given polyoxyethylene (POE) (4.2) lauryl ether, POE (10) cetyl ether, POE (30) cetyl ether, POE (10) oleyl ether, and POE (20) isostearyl ether.

Such components have effects of stably maintaining the solubilized state of the compound represented by the general formula (1) and/or a salt thereof in a high concentration region of 5% by mass or more even in a low temperature region of about 5° C. or less without impairing the steric stability in the dissolved state. In particular, in the case where the content of the compound represented by the general formula (1) and/or a salt thereof is about 10% by mass, the effects are remarkably exerted by blending the components in an amount equal to or more than the mass of the compound represented by the general formula (1) and/or a salt thereof. Therefore, it is preferred to satisfy such blending condition. Under such condition, the pharmaceutical composition for external use of the present invention shows no change in solubilizing properties when preserved for 2 weeks, preferably 1 month or more, or more preferably 3 months or more at a wide range of temperatures, including a low temperature region of about 5° C., a room temperature condition of about 20° C., and a high temperature region of about 40° C. Substantially no stereoisomer is produced, and even after preservation at 60° C. for 3 weeks, the amount of the stereoisomers is 1% by mass or less with respect to the total mass of the compound and/or a salt thereof at the beginning of preservation. Therefore, the composition is suitable for a formulation to be applied to an organ with low absorbability such as the nail. In particular, because it is rare that crystal deposition occurs through, for example, enrichment of the compound of the general formula (1) or change in solvent constitution due to evaporation after application or absorption of only a solvent into a living body, or an interfacial effect on a contact area, the absorption into the nail is not inhibited. Such effect may remarkably improve the bioavailability.

<3> Pharmaceutical Composition for External Use of the Present Invention

The pharmaceutical composition for external use of the present invention contains the above-mentioned essential components and may contain an optional component which is generally used for formulation.

For such optional component, there may be preferably exemplified: oils and waxes such as macadamia nut oil, avocado oil, corn oil, olive oil, rapeseed oil, sesame oil, castor oil, safflower oil, cottonseed oil, jojoba oil, coconut oil, palmoil, liquid lanolin, hydrogenated coconut oil, hydrogenated oil, haze wax, hydrogenated castor oil, beeswax, candelilla wax, carnauba wax, insect wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; lower alcohols such as ethanol and isopropanol; higher alcohols such as oleyl alcohol, cetyl alcohol, stearyl alcohol, isostearyl alcohol, behenyl alcohol, octyldodecanol, myristyl alcohol, and cetostearyl alcohol; synthetic ester oils such as cetyl isooctanoate, isopropyl myristate, hexyldecyl isostearate, cetyl lactate, diisostearyl malate, ethylene glycol di-2-ethyl hexanoate, neopentyl glycol dicaprate, glycerin di-2-heptyl undecanoate, glycerin tri-2-ethylhexanoate, trimethylolpropane tri-2-ethyl hexanoate, trimethylolpropane triisostearate, and pentane erythrite tetra-2-ethylhexanoate; oils such as silicone oils which are not classified into silicones, including dimethyl polysiloxane, methylphenyl polysiloxane, and modified polysiloxanes such as amino-modified polysiloxane, polyether-modified polysiloxane, alkyl-modified polysiloxane, and fluorine-modified polysiloxane; anionic surfactants such as fatty acid soaps (including sodium laurate and sodium palmitate), potassium lauryl sulfate, triethanolamine alkyl sulfate, and sodium polyoxyethylene lauryl phosphate; cationic surfactants such as stearyltrimethylammonium chloride, benzalkonium chloride, and laurylamine oxide; amphoteric surfactants such as imidazoline-based amphoteric surfactants (including a 2-cocoyl-2-imidazolinium hydroxide-1-carboxyethyloxy-2-sodium salt), betaine-based surfactants (including alkylbetaine, amidobetaine, and sulfobetaine), and acylmethyl taurine; nonionic surfactants such as sorbitan fatty acid esters (including sorbitan monostearate, sorbitan monolaurate, and sorbitan sesquioleate), glycerin fatty acids (including glycerin monostearate), propylene glycol fatty acid esters (including propylene glycol monostearate), hydrogenated castor oil derivatives, glycerin alkyl ethers, POE sorbitan fatty acid esters (including POE sorbitan monooleate, polyoxyethylene sorbitan monostearate, and polyoxyethylene sorbitan monolaurate), POE sorbit fatty acid esters (including POE-sorbit monolaurate), POE glycerin fatty acid esters (including POE-glycerin monoisostearate), POE fatty acid esters (including polyethylene glycol monooleate and POE distearate), POE alkylphenyl ethers (including POE octylphenyl ether and POE nonylphenyl ether), Pluronics, POE•POP alkyl ethers (including POE•POP 2-decyl tetradecyl ether), Tetronics, POE castor oil•hydrogenated castor oil derivatives (including POE castor oil and POE hydrogenated castor oil), sucrose fatty acid esters, and alkylglucosides; polyalcohols such as polyethylene glycol, glycerin, 1,3-butylene glycol, erythritol, sorbitol, xylitol, maltitol, gluconolactone, propylene glycol, dipropylene glycol, diglycerin, isoprene glycol, 1,2-pentanediol, 2,4-hexanediol, 1,2-hexanediol, 1,2-octanediol, polypropylene glycol, and 2-ethyl-1,3-hexanediol; moisturizing components such as sodium pyrrolidone carboxylate, lactic acid, and sodium lactate; pH adjusters such as phosphoric acid and citric acid; powders such as mica, talc, kaolin, synthetic mica, and barium sulfate which may have treated surfaces; inorganic pigments such as colcothar, yellow iron oxide, black iron oxide, cobalt oxide, ultramarine blue pigment, iron blue pigment, titanium oxide, and zinc oxide which may have treated surfaces; pearls such as mica titanium, fish scale guanine, and bismuth oxychloride which may have treated surfaces; organic pigments such as Red 202, Red 228, Red 226, Yellow 4, Blue 404, Yellow 5, Red 505, Red 230, Red 223, Orange 201, Red 213, Yellow 204, Yellow 203, Blue 1, Green 201, Violet 201, and Red 204 which may be laked; organic powders such as polyethylene powder, polymethyl methacrylate powder, nylon powder, and organopolysiloxane elastomer; UV absorbers such as p-aminobenzoic acid-based UV absorber, anthranilic acid-based UV absorber, salicylic acid-based UV absorber, cinnamic acid-based UV absorber, benzophenone-based UV absorber, sugar-based UV absorber, 2-(2'-hydroxy-5'-t-octylphenyl)benzotriazole, and 4-methoxy-4'-t-butyl dibenzoylmethane; vitamins such as vitamin A or derivatives thereof, vitamin B's including vitamin $B_6$ hydrochloride, vitamin $B_6$ tripalmitate, vitamin $B_6$ dioctanoate, vitamin $B_2$ or derivatives thereof, vitamin $B_{12}$, and vitamin $B_{15}$ or derivatives thereof, vitamin E's including α-tocopherol, β-tocopherol, γ-tocopherol, and vitamin E acetate, vitamin D's, vitamin H, pantothenic acid, pantethine, and pyrroloquinoline quinone; solvents such as aromatic alcohols such as phenylethyl alcohol, phenylpropyl alcohol, and benzyl alcohol, crotamiton, N-methyl-2-pyrrolidone, alkylene carbonates such as ethylene carbonate and propylene carbonate, diester carbonates such as diethyl carbonate and dicapryl carbonate, diesters of dibasic acids, such as diethyl sebacate, diisopropyl sebacate, diethyl adipate, and diisopropyl adipate, triacetin, and ethylene glycol salicylate; stabilizers such as hydroxy acids such as lactic acid, glycolic acid, and citric acid, and mineral acids such as phosphoric acid.

For particularly preferred components out of those optional components, there may be preferably exemplified a solvent selected from an alkylene carbonate having a cyclic structure, such as propylene carbonate, a diester carbonate typified by a dialkyl carbonate such as dicapryl carbonate in which two linear hydrocarbon groups are bonded, an aromatic alcohol such as benzyl alcohol, and a diester of a dibasic acid (provided that carbonic acid is excluded) such as adipic acid and sebacic acid, and the like.

In order to improve the stability, the pharmaceutical composition for external use of the present invention preferably contains a diester carbonate such as a dialkyl carbonate or an alkylene carbonate, preferably an alkylene carbonate, or more preferably propylene carbonate in an amount of preferably 1 to 10% by mass, more preferably 2 to 8% by mass, or particularly preferably 3 to 5% by mass with respect to the total amount of the pharmaceutical composition. Such diester carbonate has preferably 5 to 30 carbon atoms, or more preferably 6 to 25 carbon atoms in total. Such component has an effect of improving solubilization stability of luliconazole or the like at a low temperature, and also has effects of suppressing crystal deposition during preservation at 5° C. for 2 weeks, preferably 4 weeks or more and improving stability at a high temperature. The component prevents stereoisomerization even during preservation at 60° C. for 3 weeks and suppresses production of stereoisomers to 1% by mass or less. Such component is preferably contained at a mass ratio almost equal to or almost half of that of luliconazole or the like. Propylene carbonate is one of the alkylene carbonates, and other alkylene carbonates such as ethylene carbonate or diester carbonates such as diethyl carbonate and dicapryl carbonate also fall within the technical scope of the present invention because they have the same effects as that of propylene carbonate. In the case of using two or more kinds of components, the amount of the diester carbonate may be construed as the total amount of the diester carbonates.

In order to improve the solubility and stability, the pharmaceutical composition for external use of the present invention contains an aromatic alcohol, or preferably benzyl alcohol in an amount of preferably 1 to 10% by mass, more preferably 1 to 8% by mass, or particularly preferably 1 to 5% by mass with respect to the total amount of pharmaceutical composition. Such component is useful as an aid for solubilizing the compound represented by the general formula (1) and/or a salt thereof during manufacture, and has an effect of suppressing crystal deposition of the compound represented by the general formula (1) and/or a salt thereof in preservation at low temperatures. Such effect is exerted when the amount is in the above-mentioned range. Other aromatic alcohols such as phenylethyl alcohol and phenylpropyl alcohol also exert similar effects, although the effects are smaller than that of benzyl alcohol, and hence may be handled in the same way as benzyl alcohol. That is, such aromatic alcohols fall within the technical scope of the present invention.

The pharmaceutical composition for external use of the present invention contains, as a preferred component, a diester of a dibasic acid, or preferably diethyl adipate or diisopropyl adipate in an amount of preferably 1 to 20% by mass, more preferably 2 to 18% by mass, or particularly preferably 3 to 15% by mass with respect to the total amount of the pharmaceutical composition. Here, the dibasic acid means a collective name including dicarboxylic acids having two carboxyl groups but excluding carbonic acid. For such dibasic acid, adipic acid, tartaric acid, succinic acid, and sebacic acid may be suitably exemplified. For an ester moiety of which the diester of a dibasic acid is formed, there may be exemplified an alkyl group or an alkenyl group having a linear or branched structure with 1 to 20 carbon atoms, or more preferably 1 to 5 carbon atoms. To be specific, there may be suitably exemplified a methyl group, an ethyl group, an ethoxyethyl group, a propyl group, an isopropyl group, an isoprenyl group, a butyl group, a sec-butyl group, a tert-butyl group, a hexyl group, an octyl group, an isooctyl group, a decanyl group, a lauryl group, a cetyl group, a stearyl group, an isostearyl group, and an oleyl group. Such component has an action of, in the range of the above-mentioned amount, dissolving a compound represented by the general formula (1) and/or a salt thereof solvated with benzyl alcohol or the like to form a homogeneous solution system. Such action may be observed in a wide range of diesters of dibasic acids, such as diethyl sebacate and diisopropyl sebacate, although being weaker than that of diethyl adipate and diisopropyl adipate. That is, those fall within the technological scope of the present invention. For the diester of a dibasic acid, which enhances the effect of the present invention, as described above, there may be particularly preferably exemplified one having, as an acid residue, an adipic acid residue, a sebacic acid residue, or a succinic acid residue, and having, as an aliphatic group, a methyl group, an ethyl group, an ethoxyethyl group, a propyl group, an isopropyl group, a butyl group, a sec-butyl group, a tert-butyl group, an octyl group, an isooctyl group, or a lauryl group.

For the diester carbonate, and aromatic alcohol, and diester of a dibasic acid, one kind chosen therefrom may be selected, or a combination of two or more kinds may be selected. For the amount range, preferred amount ranges may be independently selected for the respective components, and those three kinds of components are preferably blended so that the total mass would be 1 to 30% by mass, or more preferably 2 to 25% by mass with respect to the total amount of the pharmaceutical composition.

Further, in order to improve the stability of the pharmaceutical composition for external use of the present invention and the effect of suppressing crystal deposition after application, a stabilizer such as a hydroxy acid including lactic acid, glycolic acid, and citric acid or a mineral acid including phosphoric acid is preferably incorporated in an amount of preferably 0.1 to 20% by mass, or more preferably 1 to 10% by mass with respect to the total amount of the pharmaceutical composition. In addition, in order to improve the solubility and stability, it is also preferred to contain a higher alcohol in a liquid state at 1 atom at 25° C., such as isostearyl alcohol, in an amount of preferably 10 to 30% by mass, or more preferably 15 to 25% by mass with respect to the total amount of the pharmaceutical composition. In addition, crotamiton or N-methyl-2-pyrroridone having an effect of maintaining steric stability is preferably incorporated in an amount of preferably 1 to 30% by mass, or more preferably 2 to 15% by mass with respect to the total amount of the pharmaceutical composition. In addition, in order to improve the solubility, it is also preferred to contain a polyalcohol such as propylene glycol, in an amount of preferably 1 to 30% by mass, or more preferably 5 to 20% by mass with respect to the total amount of the pharmaceutical composition.

The pharmaceutical composition for external use of the present invention may be manufactured by using such optional components and essential components. For a method of manufacturing the pharmaceutical composition for external use of the present invention, there may be preferably exemplified a method involving adding a part of solvent components such as an aliphatic alcohol and an aromatic alcohol to a compound represented by the general formula (1) or a salt thereof to solvate the compound or a salt thereof and adding the remainder of solvents for salvation to solubilize the compound or a salt thereof. For the above-mentioned solvents for solvation and solubilization, there may be suitably exemplified an aliphatic and aromatic alcohol are preferably used for solubilization, and a diester of a dibasic acid, acetone and a diester carbonate are preferably used for improving the solubilization. In such solubilization process, heating is preferably performed at 30 to 90° C. The amount of the above-mentioned solvents for solvation is preferably 10 to 50% by mass of the total amount of the solvents for solvation. The pharmaceutical composition for external use of the present invention may be obtained by performing the above-mentioned processes and further treatment of the resultant according to a conventional method.

The pharmaceutical composition for external use of the present invention can be formulated into any form without particular limitation as long as the form is used in a pharmaceutical composition for external use, and for example, there may be suitably given a lotion, an emulsion, a gel, a cream, an aerosol, a nail enamel, and a hydrogel patch. Of those, a lotion is particularly preferred.

The pharmaceutical composition for external use of the present invention is preferably used for treatment of mycotic diseases or prevention of progression of the diseases by using characteristics of luliconazole or the like. For the mycotic diseases, there may be exemplified: tinea pedis such as athlete's foot; tinea corporis such as candida and pityriasis versicolor; and tinea on a hard keratin portion, such as tinea unguium. Because of remarkable effects, it is particularly preferred to use the pharmaceutical composition for external use of the present invention for treatment of the hard keratin portion, such as tinea unguium. The effect of the pharmaceutical composition for external use of the present invention is particularly suitably expressed on the nail, and such effect is also expressed on typical dermatomycosis.

Therefore, a pharmaceutical composition for external use for dermatomycosis, which satisfies the configuration of the present invention, also falls within the technical scope of the present invention. For such dermatomycosis, there may be exemplified tinea such as tinea pedis, or particularly hyperkeratotic tinea which appears on the heels or the like. It is preferred to apply the pharmaceutical composition of the present invention to hyperkeratotic tinea, on which the conventional medicaments hardly exert their effects, in the above-mentioned dermatomycosis, because the effect of the present invention is remarkably expressed.

With regard to the use mode, for example, the pharmaceutical composition is applied to a diseased site one or several times a day at a preferred amount, and the treatment is preferably carried out day after day. In particular, for tinea unguium, luliconazole or the like as an effective component may be transferred into the nail in an amount that cannot be attained by a normal formulation. As a result, tinea unguium may be treated by simple external application without taking an antimycotic agent over a long period of time. In addition, recurrence and reinfection are being a major problem for tinea unguium. However, the recurrence and reinfection may be prevented by application of the pharmaceutical composition for external use of the present invention for 1 to 2 weeks after abatement of the symptom. The pharmaceutical composition for external use of the present invention exerts a preventive effect in such a mode.

As described above, the pharmaceutical composition for external use of the present invention may be a preparation having the following properties 2) and 3). Further, when the compound represented by the general formula (1) has a stereoisomer, the pharmaceutical composition may be a preparation having the following properties 1) to 3):
1) the amount of a stereoisomer of the compound and/or a salt thereof produced under a preservation condition of 60° C. for 3 weeks is 1% by mass or less with respect to the total mass of the compound and/or a salt thereof at the beginning;
2) the preparation is in a clear liquid state when preserved at a constant temperature of 20° C. immediately after manufacture; and
3) no crystal is deposited when the preparation is preserved at 5° C. for 2 weeks after manufacture.

The characteristic 1) may be determined by, for example, preserving a preparation at 60° C. for 3 weeks after manufacture, performing liquid chromatography using an optically-active stationary phase which may separate a compound of interest from optical isomers thereof to optically resolve the compound from the optical isomers, and calculating the amount of the isomers by peak areas of the optical isomers in the resultant chart.

The characteristic 2) may be assessed by, for example, keeping a preparation at a constant temperature of 20° C. after manufacture, and observing the liquid state of the preparation with the naked eye and/or under a microscope when/after the preparation having reached a constant temperature. When white turbidity, precipitation, or the like is not confirmed, or a crystal is confirmed only with a microscope or through observation under a microscope and the time-dependent growth of the crystal is not confirmed, the assessment of a clear liquid state is given. (It should be noted that, hereinafter, such state may be referred to as "a small amount of crystal deposition was confirmed.")

The characteristic 3) may be assessed by, for example, preserving a preparation at 5° C. for 2 weeks after manufacture, and observing the preparation with the naked eye and/or under a microscope. When no crystal deposition is confirmed with the naked eye and/or under a microscope, or a crystal is confirmed only with a microscope or through observation under a microscope and the time-dependent growth of the crystal is not confirmed, the assessment of no crystal deposition is given. (It should be noted that, hereinafter, such state may be referred to as "a small amount of crystal deposition was confirmed.")

The thus-obtained pharmaceutical composition for external use of the present invention has an excellent effect of maintaining its transparency over a long period of time although the composition contains a compound represented by the general formula (1) and/or a salt thereof in a high concentration. In addition, because crystal deposition after application is suppressed, inhibition of orientation and transfer of the compound to organs by the crystal is suppressed. Therefore, the composition has excellent bioavailability. Meanwhile, a sufficient amount of the compound is oriented to an organ with low drug orientation such as the nail, and hence the composition is preferred as a pharmaceutical composition for external use for the nail.

EXAMPLES

Hereinafter, the present invention is described in more detail by way of examples.

Examples 1 to 7

Pharmaceutical composition for external use of the present invention was produced in accordance with the formulations shown in Table 1 below. That is, luliconazole was wetted with a part (10 to 30% by mass) of dehydrated ethanol, lactic acid as a component for suppressing crystallization was dissolved in the remainder of dehydrated ethanol, and those were mixed and dissolved with heating (at 50° C. to 90° C.). To the mixture under heating (at 80 to 90° C.) successively added were benzyl alcohol and propylene carbonate. After confirmation of solubilization, acetone was added, the remainder of components was added, and the whole was mixed with stirring. After confirmation of solubilization, the mixture was cooled with stirring to afford Pharmaceutical compositions 1 to 5 for external use of the present invention. After preservation at 20° C. for 12 hours of those compositions, no crystal deposition was confirmed in observation with the naked eye and under a microscope, and clear solution properties were exhibited. Table 1 shows the results. Table 1 also shows observation results with the naked eye and under a microscope on the presence or absence of crystal deposition under preservation at 5° C. of those compositions, together with the generation status of optical isomers immediately after manufacture and under a preservation condition of 60° C. for 3 weeks.

A method of quantitatively determining an SE form [(S)-(E) form] is as follows:
HPLC (LC-9A manufactured by Shimadzu Corporation, HPLC conditions: column; CHIRALCEL OD-R 4.6×250 mm, column temperature; 40° C., mobile phase; a sodium perchlorate mixture (methanol/water (4:1, v/v)) solution (7→500), flow rate; 0.56 mL/min., detection; 295 nm)

Meanwhile, a method of quantitatively determining a Z form is as follows:
HPLC (LC-10VP manufactured by Shimadzu Corporation, HPLC conditions: column; Inertsil ODS-2 4.6×150 mm, column temperature; 40° C., mobile phase; a sodium 1-undecanesulfonate mixture (water/acetonitrile/acetic acid (100) (54:45:1, v/v/v)) solution (13→10000), flow rate; 1.0 mL/min., detection; 295 nm)

It should be noted that, in both of Example 6 in which propylene carbonate of Example 1 was replaced by acetone, and Example 7 in which propylene carbonate of Example 4 was replaced by acetone, an insoluble matter was confirmed on Day 1 after preservation at 20° C. after manufacture.

TABLE 1

| | Formulations (% by mass) | | | | | | |
|---|---|---|---|---|---|---|---|
| | Example 1 | Example 2 | Example 3 | Example 4 | Example 5 | Example 6 | Example 7 |
| Components | | | | | | | |
| Luliconazole | 8 | 6 | 8 | 10 | 8 | 8 | 10 |
| Acetone | 10 | 10 | 10 | 10 | 10 | 15 | 15 |
| Propylene carbonate | 5 | 5 | 5 | 5 | 3 | — | — |
| Benzyl alcohol | 2 | 2 | 2 | 2 | 2 | 2 | 2 |
| Diisopropyl adipate (DID) | — | — | — | — | — | — | — |
| Lactic acid | 4 | 4 | 6 | 6 | 6 | 4 | 6 |
| Propylene glycol | 10 | 10 | 10 | 10 | 10 | 10 | 10 |
| Dehydrated ethanol | 61 | 63 | 59 | 57 | 61 | 61 | 57 |
| Solution properties after manufacture | | | | | | | |
| 20° C. 12 hr | ○ | ○ | ○ | ○ | ○ | ○ | ○ |
| 20° C. 24 hr | ○ | ○ | ○ | ○ | ○ | Δ | Δ |
| Presence or absence of crystal deposition under preservation | | | | | | | |
| 5° C. 5 day | ○ | ○ | ○ | ○ | ○ | | |
| 5° C. 1 week | ○ | ○ | ○ | ○ | ○ | | |
| 5° C. 2 week | ○ | ○ | ○ | ○ | ○ | | |
| 5° C. 3 week | ○ | Δ | ○ | ○ | ○ | | |
| Stability Beginning | | | | | | | |
| Quantitative determination (with respect to beginning) | 100 | 100 | 100 | 100 | 100 | | |
| Purity | | | | | | | |
| SE form | 0.44 | 0.44 | 0.47 | 0.48 | 0.47 | | |
| Z form | 0.02 | 0.02 | 0.02 | 0.01 | 0.02 | | |
| Others Total amount | 0.037 | | 0.0184 | 0.0126 | 0.0061 | | |
| 60° C., 3 week | | | | | | | |
| Quantitative determination (with respect to beginning) | 100.1 | 99.4 | 101.4 | 100.9 | 100 | | |
| Purity | | | | | | | |
| SE form | 0.46 | 0.46 | 0.48 | 0.49 | 0.48 | | |
| Z form | 0.06 | 0.06 | 0.07 | 0.08 | 0.06 | | |
| Others Total amount | 0.1534 | 0.1544 | 0.1814 | 0.1747 | 0.121 | | |

Indication of solution properties; ○: no insoluble matter was confirmed, Δ: a small amount of insoluble matter was confirmed, and x: an insoluble matter was confirmed.
Indication of presence or absence of crystal deposition; ○: no crystal deposition was confirmed, and Δ: a small amount of crystal deposition was confirmed.

Comparative Example 1

Components of Table 2 below were treated, and a pharmaceutical composition for external use of Comparative Example 1 was obtained in the same method as in Example 1. It was revealed that the pharmaceutical composition had a problem in its practical use because crystal deposition was already confirmed under a constant temperature of 20° C. immediately after manufacture.

TABLE 2

| Components | Formulation (% by mass) Comparative Example 1 |
|---|---|
| Luliconazole | 10 |
| Acetone | — |
| Propylene carbonate | 5 |
| Benzyl alcohol | 2 |
| DID | — |

TABLE 2-continued

| Components | Formulation (% by mass) Comparative Example 1 |
|---|---|
| Lactic acid | 4 |
| Propylene glycol | 10 |
| Dehydrated ethanol | 69 |
| Presence or absence of crystal deposition immediately after manufacture | x (crystal deposition) |

Example 8

Components of Table 3 below were treated, and a pharmaceutical composition for external use of Example 8 was obtained in the same method as in Example 1. In the pharmaceutical composition, such crystal deposition that is less than Comparative Example 1 but was recognized only under a microscope was confirmed under a constant temperature of 20° C. immediately after manufacture. It should be noted that, when the pharmaceutical composition was preserved at 5° C., such a small amount of crystal deposition that was recognized only under a microscope was confirmed on Day 1. As long as the solubility is concerned, it was revealed that the diester of a dibasic acid exhibited a similar effect to that of diester carbonate.

TABLE 3

| Components | Formulation (% by mass) Example 8 |
|---|---|
| Luliconazole | 10 |
| Acetone | 10 |
| Propylene carbonate | — |
| Benzyl alcohol | 2 |
| DID | 12 |
| Lactic acid | 4 |
| Propylene glycol | — |
| Dehydrated ethanol | 62 |
| Presence or absence of crystal deposition immediately after manufacture | Δ (small amount of crystal deposition) |
| Presence or absence of crystal deposition under preservation 5° C. 1 day | Δ (small amount of crystal deposition) |

Example 9

Components of Table 4 below were treated, and a pharmaceutical composition for external use of Example 9 was obtained. In the pharmaceutical composition, no crystal deposition was recognized under a microscope under a constant temperature of 20° C. immediately after manufacture. It should be noted that, when the pharmaceutical composition was preserved at 5° C., there was no change in appearance on Day 1, a trace amount of crystal deposition was confirmed on Day 4, and a small amount of crystal deposition which was recognized only under a microscope was confirmed on Week 1. This revealed that it was preferred to contain propylene carbonate in terms of not only stability but also solubility. Further, an effect by addition of propylene glycol was also confirmed.

TABLE 4

| Components | Formulation (% by mass) Example 9 |
|---|---|
| Luliconazole | 10 |
| Acetone | 10 |
| Propylene carbonate | 5 |
| Benzyl alcohol | 2 |
| DID | — |
| Lactic acid | 4 |
| Propylene glycol | — |
| Dehydrated ethanol | 69 |

TABLE 4-continued

| Components | Formulation (% by mass) Example 9 |
|---|---|
| Presence or absence of crystal deposition immediately after manufacture | ○ (no. deposition was confirmed) |
| Presence or absence of crystal deposition under preservation 5° C. 1 week | Δ (small amount of crystal deposition) |

Examples 10 to 14 and Comparative Example 2

Pharmaceutical compositions for external use of the present invention were manufactured in accordance with the formulations shown in Table 5 below. That is, formulation components were heated to 70° C., luliconazole was wetted with a part (10 to 30% by mass) of dehydrated ethanol, lactic acid as a component for suppressing crystallization was dissolved in the remainder of dehydrated ethanol, and those were mixed and dissolved with heating. To the mixture successively added were benzyl alcohol and propylene carbonate. After confirmation of solubilization, to the mixture under heating, isostearyl alcohol and/or a polyoxyethylene alkyl ether, which had been mixed in advance, were gradually added to stabilize solubilizing properties, and after doing that, the remainder of components were successively added to solubilize formulation components. The solution was cooled with stirring to afford Pharmaceutical compositions 10 to 13 for external use of the present invention. After preservation at 20° C. for 12 hours of those compositions, no crystal deposition was confirmed in observation with the naked eye and under a microscope, and clear solution properties were exhibited. Table 5 shows the results. Table 5 also shows observation results with the naked eye and under a microscope on the presence or absence of crystal deposition under preservation at 5° C. of those compositions, together with the generation status of optical isomers immediately after manufacture and under a preservation condition of 60° C. for 3 weeks. A method of quantitatively determining optical isomers is the same as that as mentioned above.

It should be noted that, in Example 14 in which propylene carbonate of Example 10 was replaced by ethanol, a small amount of crystal deposition that was recognized only under a microscope was confirmed immediately after manufacture and in Comparative Example 2 in which polyoxyethylene (10) cetyl ether was replaced by ethanol, a crystal was already confirmed immediately after manufacture. Thus, it is understood that a constitution of the present invention exerts an effect of stably solubilizing luliconazole in as high a concentration as 5% by mass.

TABLE 5

| | Formulations (% by mass) | | | |
|---|---|---|---|---|
| | Example 10 | Example 11 | Example 12 | Example 13 |
| Components | | | | |
| Luliconazole | 5 | 5 | 5 | 5 |
| Polyoxyethylene (10) cetyl ether (Nikkol BC-10) | 2.5 | — | — | — |
| Polyoxyethylene (10) lauryl ether (Nikkol BL-4.2) | — | 5 | 5 | 5 |
| Polyethylene glycol (PEG) 400 | — | — | — | 20 |
| Propylene carbonate | 5 | 5 | 5 | 5 |
| Benzyl alcohol | 2 | 2 | 2 | 2 |
| DID | — | — | — | — |
| Lactic acid | 4 | 4 | 4 | 4 |

TABLE 5-continued

| | Formulations (% by mass) | | | |
|---|---|---|---|---|
| | Example 10 | Example 11 | Example 12 | Example 13 |
| Propylene glycol | 10 | 10 | 10 | 10 |
| Isostearyl alcohol | — | — | 20 | 20 |
| Dehydrated ethanol | 71.5 | 69 | 49 | 29 |
| Solution properties after manufacture | | | | |
| 20° C. 12 hr | ○ | ○ | ○ | ○ |
| 20° C. 24 hr | ○ | ○ | ○ | ○ |
| Presence or absence of crystal deposition under preservation | | | | |
| 5° C. 1 week | ○ | ○ | ○ | ○ |
| 5° C. 2 week | ○ | ○ | ○ | ○ |
| 5° C. 3 week | ○ | ○ | ○ | ○ |
| 5° C. 4 week | ○ | ○ | ○ | ○ |
| 5° C. 8 week | ○ | ○ | ○ | ○ |
| 5° C. 10 week | ○ | ○ | ○ | ○ |
| Stability | | | | |
| Beginning | | | | |
| Quantitative determination (with respect to beginning) | 100% | 100% | 100% | 100% |
| Purity    SE form | 0.3 | 0.33 | 0.32 | 0.32 |
|           Z form  | 0.01 | 0.02 | 0.01 | 0.01 |
| Others    5.4 min | — | — | — | — |
|           6.6 min | — | — | — | — |
|           9.8 min | — | — | — | — |
| 60° C., 3 week | | | | |
| Quantitative determination (with respect to beginning) | 99.5% | 99.6% | 98.6% | 97.6% |
| Purity    SE form | 0.4 | 0.41 | 0.39 | 0.4 |
|           Z form  | 0.06 | 0.06 | 0.05 | 0.09 |
| Others Total amount | 0.21 | 0.21 | 0.292 | 0.3 |

Indication of solution properties; ○: no insoluble matter was confirmed, Δ: a small amount of insoluble matter was confirmed, and x: insoluble matter was confirmed.
Indication of presence or absence of crystal deposition; ○: no crystal deposition was confirmed, and Δ: a small amount of crystal deposition was confirmed.

INDUSTRIAL APPLICABILITY

The present invention can be applied to a pharmaceutical composition for external use useful for treatment of onychomycosis.

What is claimed is:
1. A pharmaceutical composition for external use, comprising:
   (a) a compound represented by the following general formula (1) and/or a salt thereof in an amount of 5 to 15% by mass with respect to a total amount of the pharmaceutical composition;
   (b) a polyoxyethylene alkyl ether in an amount of 2 to 5% by mass with respect to a total amount of the pharmaceutical composition; and/or a polyoxyethylene alkenyl ether in an amount of 2 to 5% by mass with respect to a total amount of the pharmaceutical composition, wherein alkyl group of the polyoxyethylene alkyl ether has 8 to 30 carbon atoms, and alkenyl group of the polyoxyethylene alkenyl ether has 8 to 30 carbon atoms; and
   (c) at least one selected from the group consisting of an aromatic alcohol, and a diester of a dibasic acid, in an amount of 1 to 30% by mass with respect to a total amount of the pharmaceutical composition,
wherein the pharmaceutical composition is in the form of a clear solution, and
wherein the compound represented by the following general formula (1) is luliconazole;

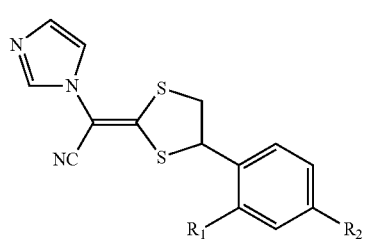

General formula (1)

wherein each of $R_1$ and $R_2$ represent a chlorine atom.
2. The pharmaceutical composition for external use according to claim 1, which has the following properties:
   (a) when the compound represented by the general formula (1) and/or a salt thereof has a stereoisomer, an amount of the stereoisomer of the compound and/or a salt thereof produced under a preservation condition of 60° C. for 3 weeks is 1% by mass or less with respect to a total mass of the compound and/or a salt thereof at beginning of preservation;
   (b) the composition is in a clear liquid state when preserved at a constant temperature of 20° C. immediately after manufacture; and
   (c) no crystal is deposited when the composition is preserved at 5° C. for 2 weeks after manufacture.

3. The pharmaceutical composition for external use according to claim 1, wherein the pharmaceutical composition is a medicament for treatment of tinea unguium.

4. A method for treatment of tinea unguium comprising administering the pharmaceutical composition of claim 1 in an effective amount to an individual in need thereof.

5. The pharmaceutical composition for external use according to claim 1, further comprising acetone in an amount of 1 to 30% by mass with respect to a total amount of the pharmaceutical composition.

* * * * *